United States Patent
Boutinon et al.

(10) Patent No.: US 10,492,676 B2
(45) Date of Patent: Dec. 3, 2019

(54) PHOROPTER, AND METHOD FOR MEASURING REFRACTION USING A PHOROPTOR OF SAID TYPE

(71) Applicant: ESSILOR INTERNATIONAL (COMPAGNIE GENERALE D'OPTIQUE), Charenton-le-Pont (FR)

(72) Inventors: Stephane Boutinon, Charenton-le-Pont (FR); Vincent Tejedor Del Rio, Charenton-le-Pont (FR); Michel Nauche, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 15/302,379

(22) PCT Filed: Apr. 7, 2015

(86) PCT No.: PCT/FR2015/050892
§ 371 (c)(1),
(2) Date: Oct. 6, 2016

(87) PCT Pub. No.: WO2015/155458
PCT Pub. Date: Oct. 15, 2015

(65) Prior Publication Data
US 2017/0027435 A1 Feb. 2, 2017

(30) Foreign Application Priority Data
Apr. 8, 2014 (FR) .................................. 14 53129

(51) Int. Cl.
*A61B 3/00* (2006.01)
*A61B 3/028* (2006.01)
(Continued)

(52) U.S. Cl.
CPC .......... *A61B 3/0285* (2013.01); *A61B 3/0075* (2013.01); *A61B 3/028* (2013.01); *A61B 3/036* (2013.01); *G02B 3/0081* (2013.01)

(58) Field of Classification Search
CPC ... A61B 3/0075; A61B 3/0083; A61B 3/0285; A61B 3/0041; A61B 3/005; A61B 3/02;
(Continued)

(56) References Cited

U.S. PATENT DOCUMENTS 3,408,137 A * 10/1968 Reiner ................. A61B 3/0285
351/222
4,099,141 A 7/1978 Leblanc et al.
(Continued)

FOREIGN PATENT DOCUMENTS

CN 1745327 A 3/2006
CN 101094605 A 12/2007
(Continued)

OTHER PUBLICATIONS

International Search Report, dated Jul. 16, 2015, from corresponding PCT application.
(Continued)

*Primary Examiner* — Jordan M Schwartz
(74) *Attorney, Agent, or Firm* — Young & Thompson (57) ABSTRACT

A refractor (100) includes: an enclosure having a front face containing a first optical window and a back face containing a second optical window aligned with the first optical window along an optical axis of observation; and at least one vision compensating device making it possible to observe along the optical axis of observation. The vision compensating device includes, between the first window and the second window, a first optical element having a spherical power along the optical axis, the spherical power being variable. The enclosure is mounted on an orientable holder
(Continued)

(104) that is rotatable relative to a stationary portion (102) about a horizontal axis (H). A method for measuring refraction employing such a refractor is also disclosed.

18 Claims, 5 Drawing Sheets

(51) Int. Cl.
*A61B 3/036* (2006.01)
*G02B 3/00* (2006.01)

(58) Field of Classification Search
CPC ...... A61B 3/028; A61B 3/036; G02B 3/0081; G02B 3/14; G02B 26/004; G02B 26/005
See application file for complete search history.

(56) References Cited

U.S. PATENT DOCUMENTS

| | | | | |
|---|---|---|---|---|
| 4,105,302 A | * | 8/1978 | Tate, Jr. .................. | A61B 3/028 351/210 |
| 4,940,323 A | * | 7/1990 | Downing ............... | A61B 5/161 351/203 |
| 5,223,864 A | | 6/1993 | Twisselmann | |
| 2004/0032568 A1 | * | 2/2004 | Fukuma .................. | A61B 3/04 351/233 |
| 2004/0156021 A1 | * | 8/2004 | Blum .................... | A61B 3/0285 351/233 |
| 2004/0263782 A1 | * | 12/2004 | Jones ................... | A61B 3/0285 351/221 |
| 2005/0105044 A1 | * | 5/2005 | Warden ................ | A61B 3/1015 351/159.08 |
| 2006/0050238 A1 | * | 3/2006 | Nakamura ........... | A61B 3/0041 351/205 |
| 2006/0106426 A1 | * | 5/2006 | Campbell ............ | G02B 26/004 607/3 |
| 2006/0170864 A1 | * | 8/2006 | Kuiper .................. | A61B 3/028 351/205 |
| 2010/0202054 A1 | * | 8/2010 | Niederer ................ | G02B 3/14 359/558 |
| 2013/0027783 A1 | * | 1/2013 | Greiner ................ | F41G 7/2253 359/648 |
| 2014/0055747 A1 | * | 2/2014 | Nistico ................... | A61B 3/14 351/206 |
| 2018/0263488 A1 | * | 9/2018 | Pamplona ................ | A61B 3/09 |

FOREIGN PATENT DOCUMENTS

| | | |
|---|---|---|
| CN | 101966074 A | 2/2011 |
| EP | 1882444 A1 | 1/2008 |
| EP | 2 034 338 A | 3/2009 |
| JP | S51-123093 | 10/1976 |
| JP | H03-123532 | 5/1991 |
| JP | 6-125873 * | 5/1994 |
| JP | 06125873 A | 5/1994 |
| JP | H06-181888 | 7/1994 |
| JP | 2004-073412 | 3/2004 |
| JP | 2005-342187 | 12/2005 |
| JP | 2008-251061 | 6/2008 |
| JP | 4826988 B1 | 11/2011 |
| JP | 2012239701 A | 12/2012 |
| WO | 2004/072687 A2 | 8/2004 |
| WO | 2012/123549 A1 | 9/2012 |

OTHER PUBLICATIONS

Chinese Office Action issued in Application No. 201510161809.7, dated Jan. 22, 2017 with English translation.

* cited by examiner

PHOROPTER, AND METHOD FOR MEASURING REFRACTION USING A PHOROPTOR OF SAID TYPE

TECHNICAL FIELD OF THE INVENTION

The present invention relates to the field of optometry.

It more particularly relates to a refractor, and a method for measuring refraction using such a refractor.

PRIOR ART

In the context of the measurement of the visual acuity of a patient, it has already been proposed to simulate the visual compensation to be provided, for example by means of trial frames or a refractor such as a refraction head.

Trial frames are able to receive, in succession, trial lenses providing different corrections, until a suitable correction for the patient is found.

This solution is impractical and requires trial lenses to be stored separately in dedicated boxes. It furthermore involves lens changes, resulting in undesired and non-continuous transitions in corrective power.

In refraction heads, trial lenses are placed on a plurality of discs that are rotated manually or using a motorized mechanism.

However, it will be understood that such an object has a substantial bulk and weight related to the number of lenses placed on each disc. Thus, the refraction head is necessarily mounted on a rigid holder, with a substantially horizontal observation direction.

Such an apparatus is therefore not suitable for precisely establishing the near-vision correction required by the patient. Specifically, with such an apparatus, the visual axis remains approximately horizontal even while the practitioner is measuring the required near-vision correction. In contrast, in a natural near-vision position the visual axis is oriented downward by 30°, leading to a slightly different ametropia to that observed with the visual axis horizontal because of the different position of the eye and oculomotor muscles.

SUBJECT OF THE INVENTION

In this context, the present invention provides a refractor comprising an enclosure comprising a front face containing a first optical window and a back face containing a second optical window aligned with the first optical window along an optical axis of observation, and at least one vision compensating device making it possible to observe along the optical axis of observation, characterized in that the vision compensating device comprises, between the first window and the second window, a first optical element having a spherical power along the optical axis, said spherical power being variable, and in that the enclosure is mounted on an orientable holder that is rotatable relative to a stationary portion about a horizontal axis.

The vision compensating device, which especially allows spherical power along the observation axis to be varied, is housed between the first window and the second window formed in the enclosure, which, for its part, may be rotated about the horizontal axis.

Thus a compact orientable assembly is obtained allowing visual acuity measurements to be carried out in a position that is natural for the patient, in particular for far vision, intermediate vision and near vision.

The vision compensating device may furthermore be designed to generate a cylindrical correction of variable cylinder axis and of variable power. For example, the vision compensating device comprises a second optical element of cylindrical power and a third optical element of cylindrical power, the second optical element and the third optical element being rotatably adjustable about the optical axis independently of each other.

The lens of variable spherical power is for example a deformable lens containing a fluid, or, in other words, a lens containing a fluid and a deformable membrane.

The enclosure is for example mounted on an arm hinged relative to the orientable holder about an axis perpendicular to the horizontal axis, thereby allowing the convergence of the optical axis of observation to be varied and this convergence to be matched to the tested vision (far vision or near vision), as explained in the description below.

The enclosure may furthermore be mounted on the orientable holder in a position that is adjustable along the horizontal axis. Precisely, in the example described below, the enclosure is mounted in an adjustable position on the hinged arm.

A wheel may also be provided, said wheel being rotatably mounted in the enclosure about an axis parallel to the optical axis and bearing at least one complementary element intended to be placed in front the optical axis. The complementary element may be a filter, a prism, an aperture or a shield.

The refractor may comprise means for movably mounting a diasporameter on the front face of the enclosure in a first position, in which at least one prism of the diasporameter is aligned with the optical axis, and in a second position, in which the diasporameter leaves free the first optical window.

As explained in the description below, the enclosure may have a lower face such that the distance, in projection onto a vertical plane, between the optical axis and this lower face is smaller than or equal to 30 mm or even than 20 mm. Thus, the bulk of the enclosure is restricted in the region located under the eyes of the user and the enclosure does not interfere with the face of the user during its rotation about the horizontal axis.

The position of the orientable holder is for example rotatably adjustable about the horizontal axis by means of an actuator. As a variant, this positional adjustment could be carried out manually.

Provision may furthermore be made for the stationary portion to comprise means for positioning a portion of the head of a user (generally designated a "forehead rest").

The stationary portion is for example dimensioned so that said horizontal axis passes through the eyes of said user (when the latter positions his head on said positioning means). More precisely, the stationary portion is for example dimensioned so that said horizontal axis passes through the centre of rotation of at least one eye of said user. Thus, the movement of the orientable holder corresponds to the possible movement of the eye, for example when it passes from a far-vision observation to a near-vision observation.

The refractor may also comprise at least one image capturing device having a line of sight; the image capturing device may then be mounted in the refractor so that the line of sight is essentially parallel to said horizontal axis, thereby especially allowing the location of the eye relative to the vision compensating device to be continuously monitored.

The image capturing device may then be designed to measure the distance between the eye and the vision compensating device. Provision may then be made to set the spherical power of the first optical element depending on the measured distance.

The invention also provides a method for measuring refraction by means of a refractor such as described above, comprising the following steps:

- inclining the orientable holder relative to the stationary portion;
- adjusting the spherical power of the first optical element; and
- storing the adjusted spherical power in memory, for example in association with the aforementioned inclination.

As indicated above, the spherical power may then be adjusted depending on a distance between an eye of a user and the vision compensating device, which distance is measured by an image capturing device.

BRIEF DESCRIPTION OF THE DRAWINGS

The following description, given with regard to the appended drawings and by way of nonlimiting example, will allow what the invention consists of and how it can be carried out to be well understood.

In the appended drawings.

DETAILED DESCRIPTION OF AN EXAMPLE EMBODIMENT

Figures 1, 2, 5:
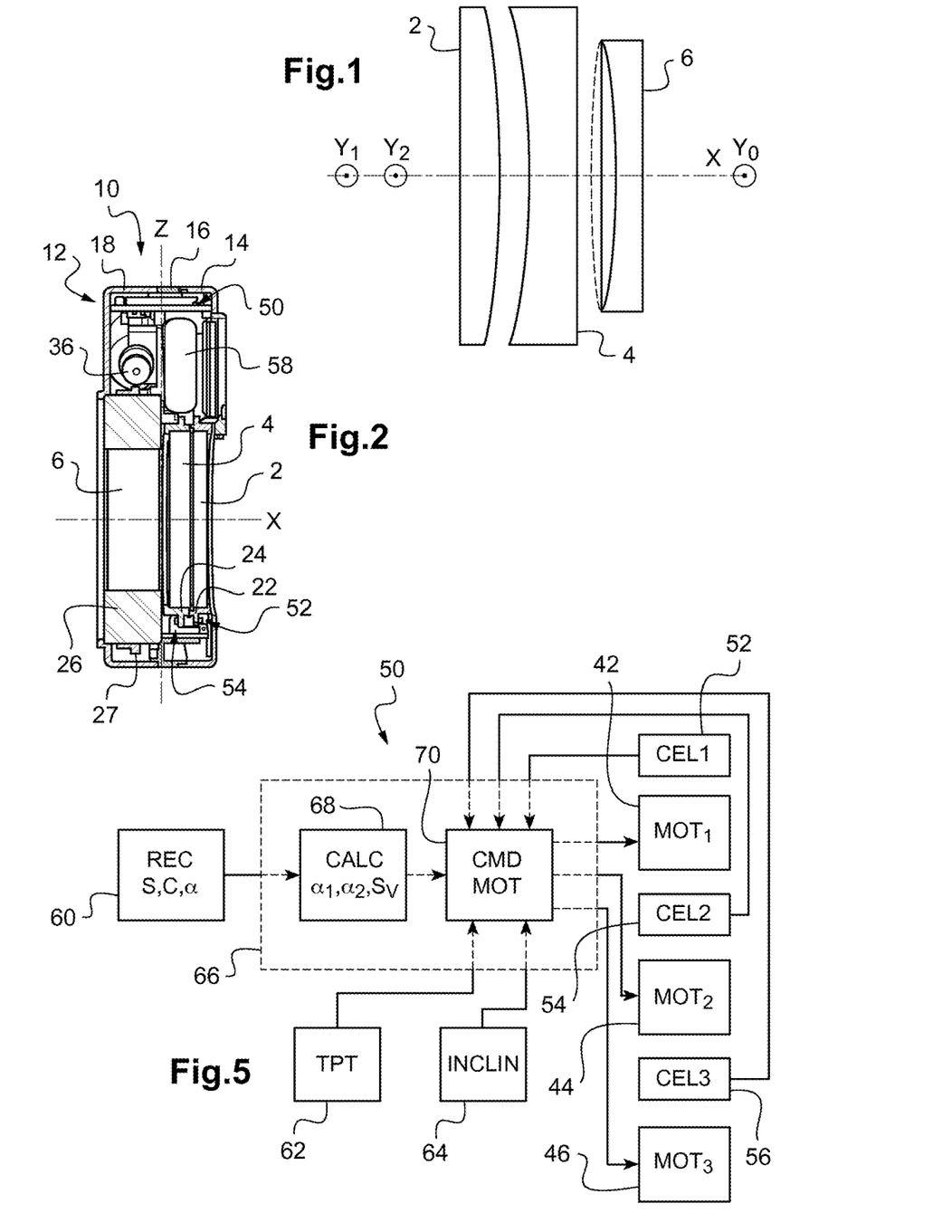
FIG. 1 schematically shows the optical elements used in one example implementation of the invention.
FIG. 2 shows a cross-sectional view of an example vision compensating device that may be used in the context of the invention.
FIG. 5 schematically shows an element for controlling the vision compensating device in FIG. 2.

FIG. 1 schematically shows the main optical elements of an example vision compensating device used, as described below, in a refractor according to the teachings of the invention.

These optical elements comprise a convex planar-cylindrical lens 2 of cylindrical power $C_0$, a concave planar-cylindrical lens 4 of negative cylindrical power $-C_0$, and a lens 6 of variable spherical power $S_V$.

The absolute value (or modulus), here $C_0$, of the cylindrical power (here $-C_0$) of the concave planar-cylindrical lens 4 is therefore equal to the absolute value ($C_0$) (or modulus) of the cylindrical power ($C_0$) of the convex planar-cylindrical lens 2.

As a variant, provision could be made for the respective cylindrical powers of the concave planar-cylindrical lens 4 and the convex planar-cylindrical lens 2 to be (slightly) different in absolute value, but they are in any case such that the resulting cylindrical power generated by combining these two lenses has a negligible value (for example smaller than 0.1 dioptres in absolute value) in at least one relative position of these two lenses.

The three lenses 2, 4, 6 are placed on the same optical axis X. Precisely, each of the three lenses 2, 4, 6 has a generally cylindrical exterior shape centred on the optical axis X. In the example described here, the lenses 2, 4, 6 have the following diameters (quantifying their bulk), respectively: 25 mm, 25 mm, 20 mm.

Thus, it will be noted that it is preferable to use this vision compensating device 10 with the eye of the patient located on the side of the variable spherical power lens 6 so that the lenses 2, 4 of cylindrical power, which are larger in diameter, do not limit the field of view defined by the variable spherical power lens 6, which itself is perceived as wide due to its proximity to the eye of the patient.

Each of the three lenses 2, 4, 6 comprises a first planar face, perpendicular to the optical axis X, and a second face opposite the first face and optically active:

- the optically active face of the lens 2 is cylindrically convex in shape (the axis $Y_1$ of the cylinder defining this face lying perpendicular to the optical axis X);
- the optically active face of the lens 4 is cylindrically concave in shape (the axis $Y_2$ of the cylinder defining this face lying perpendicular to the optical axis X); and
- the optically active face of the lens 6 of variable spherical power $S_V$ is deformable and may thus adopt a convex spherical shape (as illustrated by the dotted line in FIG. 1), a planar shape or a concave spherical shape (as illustrated by the solid line).

The lens 6 of variable spherical power $S_V$ is for example a lens of the type described in document EP 2 034 338. Such a lens comprises a cavity closed by a transparent deformable membrane and a planar movable transparent wall; the cavity contains a transparent liquid of constant volume that is strained, to a greater or lesser degree, by the movable face, in order to deform the membrane that is thus either a spherical concave surface, or a planar surface, or a spherical convex surface. In the lens used, a transmission made up of a nut/bolt system ensures transformation of rotary to linear motion. Thus, rotating a ring mounted on a casing 26 translates a part of the lens 6, thereby causing the aforementioned deformation of the transparent membrane, as explained for example in the aforementioned document EP 2 034 338. It is thus possible to vary the spherical power $S_V$ continuously via mechanical action on the lens 6. In the example described here, the lens 6 has a focal length variable between −40 mm and 40 mm, namely a spherical power $S_V$ variable between −25 D and 25 D (D being one dioptre, the unit of measurement of refractive power, the inverse of focal length expressed in metres).

Moreover, the planar-cylindrical lenses 2, 4 have, as already indicated, cylindrical powers of $-C_0$ and $C_0$, respectively, with here $C_0=5$ D.

As explained in greater detail below, the concave planar-cylindrical lens 4 and the convex planar-cylindrical lens 2 are rotationally mounted about the axis X (rotation centred on the axis X).

The axis $Y_1$ of the convex cylinder formed on the optically active face of the convex planar-cylindrical lens 2 may thus make a variable angle $\alpha_1$ with a reference axis $Y_0$ (which is fixed and perpendicular to the optical axis X).

Likewise, the axis $Y_2$ of the concave cylinder formed on the optically active face of the concave planar-cylindrical lens 4 may make a variable angle $\alpha_2$ with the reference angle $Y_0$.

By calculating refractive power on the various meridians, the following formulae are obtained for the spherical power S, the cylindrical power C and the angle of astigmatism $\alpha$ of the optical subassembly formed from the three optical elements 2, 4, 6 just described:

$$\tan 2\alpha = \frac{\sin 2\alpha_2 - \sin 2\alpha_1}{\cos 2\alpha_2 - \cos 2\alpha_1} = -\frac{\cos(\alpha_1 + \alpha_2)}{\sin(\alpha_1 + \alpha_2)} \quad \text{(formula 1)}$$

$$C = C_0(\cos 2(\alpha - \alpha_2) - \cos 2(\alpha - \alpha_1)) \quad \text{(formula 2)}$$

$$S = S_V - \frac{C}{2}. \quad \text{(formula 3)}$$

It will be noted that the term (−C/2) in formula 3 corresponds to a spherical power generated by the resultant of the 2 lenses providing cylindrical power.

By setting the rotational position of the convex planar-cylindrical lens 2 and the rotational position of the concave planar-cylindrical lens 4 independently of each other, as described below, it is possible to vary, independently, each of the angles $\alpha_1$ and $\alpha_2$ from 0° to 360° and thus obtain a cylindrical power C adjustable between −2·$C_0$ and 2·$C_0$ (i.e. here between −10 D and 10 D) for any angle of astigmatism adjustable between 0° and 360° by controlling the two lenses simultaneously. As formula 3 indicates, the spherical power resulting from the resultant of the orientation of the 2 cylindrical lenses is compensated for using the lens of variable spherical power.

Moreover, by varying the spherical power $S_V$ of the spherical lens 6, it is possible to adjust the spherical power S of the subassembly formed from the three lenses 2, 4, 6.

According to one envisionable variant, the lenses providing a set cylindrical power could have the same (positive or negative) cylindrical power $C_0$: it could be a question of two, optionally identical, convex planar-cylindrical lenses or, as an alternative, of two, optionally identical, concave planar-cylindrical lenses.

Specifically, in this case, the spherical power S, the cylindrical power C and the angle of astigmatism $\alpha$ of the subassembly formed from these two lenses and from a lens providing variable spherical power are given by the following formulae:

$$\tan 2\alpha = \frac{\sin 2\alpha_2 + \sin 2\alpha_1}{\cos 2\alpha_2 + \cos 2\alpha_1} \quad \text{(formula 4)}$$

$$C = C_0(\cos 2(\alpha - \alpha_2) + \cos 2(\alpha - \alpha_1)) \quad \text{(formula 5)}$$

$$S = S_V + C_0 - \frac{C}{2}. \quad \text{(formula 6)}$$

The term $C_0$−C/2 corresponds to the spherical power induced by the combination of two lenses providing cylindrical power.

It is therefore also possible in this case to adjust the spherical power S, the cylindrical power C and the angle of astigmatism $\alpha$, in particular so that the cylindrical power C is zero, by rotating the lenses providing cylindrical power (independently of each other) and by varying the spherical power of the lens providing variable spherical power.

An example vision compensating device 10 that uses the optical elements that have just been described is shown in FIG. 2.

Sometimes in the following description, in order to clarify the explanation, terms such as "upper" or "lower" will be used, which define an orientation in FIGS. 2, 3 and 4. It will be understood that this orientation is not necessarily applicable to the use that will possibly be made of the described device, in particular the use shown in FIGS. 6 to 12.

The vision compensating device 10 comprises a casing 12 formed from a first portion 14, a second portion 16 and a third portion 18, which are placed in succession along the optical axis X and assembled pairwise in planes perpendicular to the optical axis X.

A first toothed wheel 22 is rotatably mounted centred on the optical axis X in the first portion 14 of the casing 12 and bears, at its centre, in an aperture provided for this purpose, the convex planar-cylindrical lens 2. The first toothed wheel 22 and the convex planar-cylindrical lens 2 are coaxial; in other words, in cross section in a plane perpendicular to the optical axis X, the exterior circumference of the first toothed wheel 22 and the circumference of the convex planar-cylindrical lens 2 form concentric circles centred on the optical axis X.

Likewise, a second toothed wheel 24 is rotatably mounted centred on the optical axis X in the second portion 16 of the casing 12 and bears, at its centre, in an aperture provided for this purpose, the concave planar-cylindrical lens 4. The second toothed wheel 24 and the concave planar-cylindrical lens 4 are coaxial; in other words, in cross section in a plane perpendicular to the optical axis X, the exterior circumference of the second toothed wheel 24 and the circumference of the concave planar-cylindrical lens 4 form concentric circles centred on the optical axis X.

A third toothed wheel 27 is rotatably mounted centred on the optical axis X in the third portion 18 of the casing 12. The third toothed wheel 27 is securely fastened to the ring provided on the circumference of the casing 26 that bears the lens 6 of variable spherical power and allowing the spherical power $S_V$ to be controlled. The casing 26 of the lens 6 of variable spherical power is mounted in the third portion 18 of the casing 12.

Figure 3:
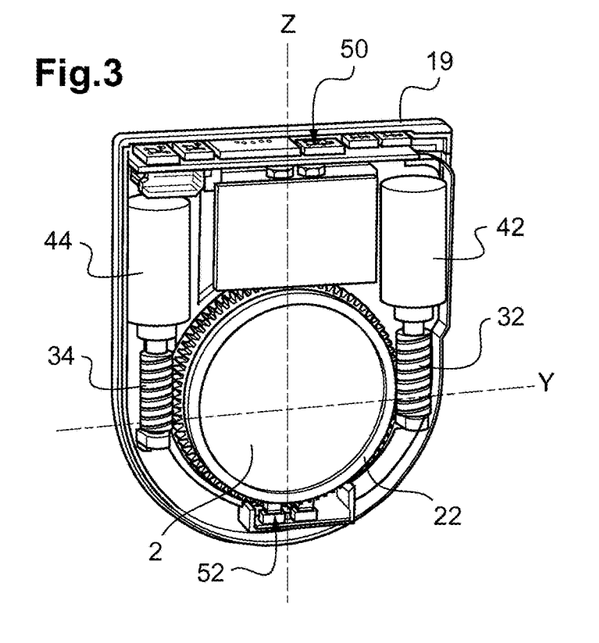
FIG. 3 shows a cutaway view of the vision compensating device in FIG. 2, on the cylindrical lens side.

As may be clearly seen in FIG. 3, the first toothed wheel 22 is rotated (about the optical axis X) by means of a first motor 42 a drive axis of which bears a first grub screw 32 that engages with the first toothed wheel 22. The first motor 42 is for example mounted in the first portion 14 of the casing 12.

The current position of the first toothed wheel 22 is monitored by a first optical cell 52.

Likewise, the second toothed wheel 24 is rotated about the optical axis X by means of a second motor 44 a drive axis of which bears a second grub screw 34 that engages with the second toothed wheel 24. The second motor 44 is for example mounted in the second portion 16 of the casing 12.

The current position of the second toothed wheel 24 is monitored by a second optical cell 54.

Figure 4:
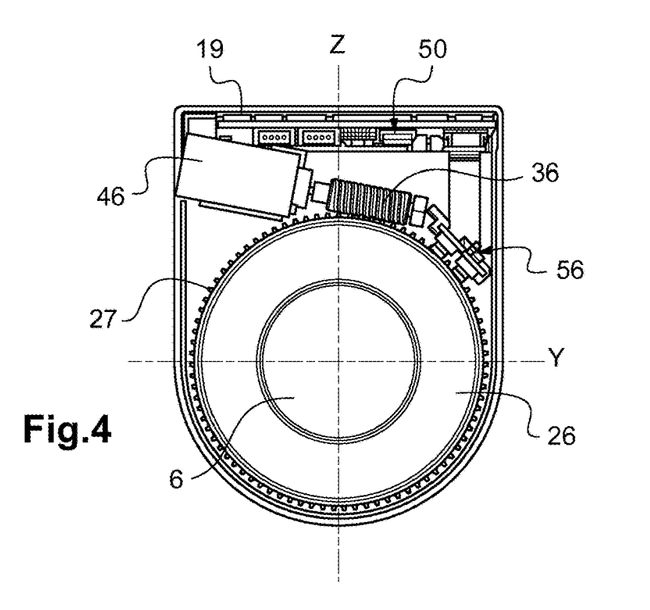
FIG. 4 shows a cutaway view of the vision compensating device in FIG. 2, on the variable spherical lens side.

As shown in FIG. 4, the third toothed wheel 27 is for its part rotated (about the optical axis X) by means of a third motor 46 that has a drive axis on which a third grub screw 36 that engages with the third toothed wheel 27 is mounted. The third motor 46 is for example mounted in the third portion 18 of the casing 12.

The current position of the third toothed wheel 27 is monitored by a third optical cell 56.

Each optical cell 52, 54, 56 is for example formed from a couple of elements comprising at least one optical sensor; the other element of the pair is for example an optical emitter (or, as a variant, a reflective element, in which case an optical emitter is associated with the optical sensor).

The first, second and third motors 42, 44, 46 are for example stepper motors having a resolution of 20 steps/turn, here set in 8ths of a step (referred to as micro-steps below). As a variant, these motors could be set in 16ths of a step.

By virtue of the construction described below, the optical elements (i.e. the first optical element, the second optical element and the lens) are mounted (in the vision compensating device) so that they (each) preserve their respective setpoint positions (even) without electrical power.

The internal volume of the casing 12 (and moreover the internal volume of each of the first, second and third portions 14, 16, 18 in the same way) may be subdivided into a space for receiving the motors 42, 44, 46 (upper region of the casing 12 in the FIGS. 2, 3 and 4) and a space for receiving the optical elements 2, 4, 6 (lower region of the casing 12 in FIGS. 2, 3 and 4).

The space for receiving the motors 42, 44, 46 has an essentially parallelepipedal shape open (toward the bottom in the figures) in the direction of the space for receiving the optical elements 2, 4, 6 and closed at the opposite end (toward the top in the figures) by an upper face 19 of the casing 12 (the upper face 19 of the casing 12 being formed by the assembled upper faces of the first, second and third portions 14, 16, 18 of the casing 12, respectively).

The arrangement of the motors 42, 44 and 46 is such as to advantageously make it possible to use a circular geometry over 180°, said circular geometry being centred on the optical axis as close as possible to the useful radius of the lenses.

The space for receiving the optical elements 2, 4, 6 has, in contrast to the space for receiving the motors, a cylindrical shape (bounded by the walls of the casing 12) that matches that of the third toothed wheel 27 over half the circumference of the latter.

In other words, the casing 12 (and therefore each of the first, second and third portions 14, 16, 18 of the casing 12) has, in the space for receiving the optical elements 2, 4, 6, a cylindrical shape with a diameter (perpendicular to the optical axis X) that is about the same as, and slightly larger than, that of the third toothed wheel 27.

The respective diameters of the toothed wheels 22, 24, 27 are chosen so as to preserve field despite the thickness of the optical subassembly.

The first motor 42 and the first grub screw 32 extend in the casing 12 in a direction Z perpendicular to the upper face of the casing 12 (and therefore especially perpendicular to the optical axis X) in such a way that the first motor 42 is housed in the space for receiving the motors whereas the first grub screw 32 lies in the space for receiving the optical elements.

As for the second motor 44 and the second grub screw 34, they extend in the casing 12 in the same direction, but opposite the first motor 42 and the first grub screw 34 relative to the cylindrical power lenses 2, 4. The second motor 44 is housed in the space for receiving the motors whereas the second grub screw 34 lies in the space for receiving the optical elements.

Thus, it will be noted that the first grub screw 32 and the second grub screw 34 are located on either side of the assembly formed by the first toothed wheel 22 and the second toothed wheel 24, and that the lateral bulk (along an axis Y perpendicular to the aforementioned axes X and Z) of these various parts (first grub screw 32, second grub screw 34, first or second toothed wheel 22, 24) is smaller than the diameter of the third toothed wheel 27 so that the first and second grub screws 32, 34 are contained in the space for receiving the optical elements without extra room being required to receive them.

Moreover, the first and second motors 42, 44 each have a bulk along the optical axis X larger than that of each of the first and second toothed wheels 22, 24, and even larger than that of each of the first and second portions 14, 16 of the casing 12. However, because these first and second motors 42, 44 are placed as indicated above on each side of the casing 12 (relative to the axis Z), they may each occupy a space that extends, along the optical axis X, in line with the first portion 14 and the second portion 16 of the casing 12.

For example, each of the first and second motors 42, 44 has a lateral bulk (outside diameter of the motor) comprised between 6 and 12, for example 10 mm, whereas the first and second toothed wheels 22, 24 each have a thickness (bulk along the axis X) comprised between 1 and 4, for example 2.5 mm.

The third motor 46 and the third grub screw 36 are in contrast located in the space for receiving the motors, in the region that extends along the axis X in line with the third portion 18 of the casing 12. Thus, the third grub screw 36 engages with the third toothed wheel 27 in an upper portion of the latter, thereby making possible for the casing 12 to follow closely the shape of the casing 12 in the lower portion of the third toothed wheel 27, as indicated above.

In the example described, as shown in FIG. 4, the axis of the third motor 46 and the third grub screw 36 is slightly inclined relative to the upper face of the casing 12 (precisely relative to the aforementioned axis Y).

Provision may for example be made for the thickness of the third toothed wheel 27 to be comprised between 0.3 mm and 2 mm.

This arrangement of the various elements allows a relatively thin casing to be obtained, typically having a thickness comprised between 15 and 20 mm.

The casing 12 also comprises, for example in the upper region of the space for receiving the motors, a control element 50, here formed of a plurality of integrated circuits borne by a common printed circuit board.

Moreover a device for storing electrical power, here a battery 58 (though, as a variant, it could be a supercapacitor), is provided in order to make the apparatus standalone. Provision may for example also be made for contactless elements for recharging the power storing device 58. The battery 58 especially allows the motors 42, 44, 46 and the control element 50 to be supplied with electrical power.

The main elements of such a control element 50, and their connections to the aforementioned motors 42, 44, 46 and to the aforementioned optical cells 52, 54, 56, are schematically shown in FIG. 5.

The control element 50 comprises a receiving module 60 designed to receive, here via a wireless link, setpoint information, i.e. information indicating the values desired by the user for the spherical power S, the cylindrical power C and the angle of astigmatism α that define the compensation generated by the optical subassembly formed from the optical elements 2, 4, 6.

The receiving module 60 is for example an infrared receiving module that receives this setpoint information from an infrared emitting remote control controlled by the user. As a variant, provision could be made for this setpoint information to be received from a personal computer via a wireless link, for example a local wireless network; the user could in this case choose values of spherical power S, cylindrical power C and angle of astigmatism α for the vision compensating device by interactive selection on the computer.

In the example application described below with reference to FIGS. 6 to 12, the setpoint information may for example be received by the electronic control board 160 via the emitter/receiver device 156.

The receiving module 60 transmits the setpoint information S, C, α received to a computing machine 66 (for example consisting of a processor executing a computer program so as to perform the functions of the computing machine, as described below), precisely to a computational module 68 controlled by the computing machine 66.

The computational module 68 computes the values of the angles $\alpha_1$, $\alpha_2$ and the value of the spherical power $S_V$ required in order to obtain the setpoint values S, C, α received as input, using the formulae given above. In the case where the planar-cylindrical lenses 2 and 4 have a cylindrical power of $-C_0$ and $C_0$, respectively, the following formulae may for example be used:

$$\begin{cases} \alpha_1 = \alpha - \frac{1}{2}\arcsin\left(\frac{C}{2C_0}\right) + \frac{\pi}{4} \\ \alpha_2 = \alpha + \frac{1}{2}\arcsin\left(\frac{C}{2C_0}\right) + \frac{\pi}{4} \end{cases}$$

$$S_V = S + \frac{C}{2}$$

The computing machine 66 also comprises a control module 70 that receives as input the values of the angles $\alpha_1$, $\alpha_2$ and spherical power $S_V$ calculated by the computational module 68 and emits control signals to the motors 42, 44, 46, in order to control each of the motors 42, 44, 46 independently of the others and obtain respective positions for the toothed wheels 22, 24, 27 that allow the desired values to be obtained:

the control module 70 controls the first motor 42 so as to make the first toothed wheel 22 turn about the optical axis X as far as a position in which the axis $Y_1$ of the optically active cylindrical surface of the convex planar-cylindrical lens 2 (borne by the first toothed wheel 22) makes an angle $\alpha_1$ with the reference direction $Y_0$;

the control module 70 controls the second motor 44 so as to make the second toothed wheel 24 turn about the optical axis X as far as a position in which the axis $Y_2$ of the optically active cylindrical surface of the concave planar-cylindrical lens 4 (borne by the second toothed wheel 24) makes an angle $\alpha_2$ with the reference direction $Y_0$; and the control module 70 controls the third motor 46 so as to make the third toothed wheel 27 turn about the optical axis X as far as a position in which the control ring of the variable spherical power sets the spherical power $S_V$ to the power calculated by the computational module 68.

The position of each toothed wheel 22, 24, 27 is known at each instant by virtue of the optical cells 52, 54, 56, respectively, which each measure, on the toothed wheel with which each is associated, the number of teeth that have passed by the optical cell relative to a reference point on the circumference of the wheel in question (for example a point devoid of teeth).

In the example described here, the first motor 42/first grub screw 32/first toothed wheel 22 assembly, just like the second motor 44/second grub screw 34/second toothed wheel 24 assembly, has a gear ratio such that one turn of the toothed wheel 22, 24 corresponds to 15040 micro-steps of the associated motor 42, 44. The resolution (angle of rotation of the toothed wheels 22, 24 for one microstep) is therefore 0.024° for the angles $\alpha_1$ and $\alpha_2$.

The third motor 46/third grub screw 36/third toothed wheel 46 assembly for its part has a gear ratio of 16640 micro-steps per turn. The ring that controls the variable spherical power can be adjusted over an angular range of 120° (therefore corresponding to 5547 micro-steps) in order to obtain the spherical power variation of −25 D to 25 D (i.e. a range of variation of 50 D). The resolution (variation in spherical power $S_V$ per micro-step) is therefore 0.009 D.

Provision may be made, during passage from initial setpoint values $\alpha_1$, $\alpha_2$, $S_V$ to new setpoint values $\alpha'_1$, $\alpha'_2$, $S'_V$, for each of the first, second and third motors 42, 44 and 46 to be actuated for a given length of time T (in seconds) that may optionally depend on the amplitude of one of the setpoint changes (for example on the variation, in absolute value, in spherical power $|S'_V - S_V|$, where |x| is the absolute value of x).

To do this, the computing machine 66 for example determines the number $p_1$ of micro-steps of the motor 42 allowing passage from the angle $\alpha_1$ to the angle $\alpha'_1$, the number $p_2$ of micro-steps of the motor 44 allowing passage from the angle $\alpha_2$ to the angle $\alpha'_2$ and the number $p_3$ of micro-steps of the motor 46 allowing passage from the spherical power $S_V$ to the spherical power $S'_V$. The computing machine 66 then commands the motor 42 to rotate at a speed of $p_1/T$ micro-steps per second, the motor 44 to rotate at a speed of $p_2/T$ micro-steps per second and the motor 46 to rotate at a speed of $p_3/T$ micro-steps per second.

The control element 50 also comprises a temperature sensor 62, which delivers information on measured ambient temperature, and an inclinometer 64, for example taking the form of an accelerometer, which delivers information on the orientation of the vision compensating device 10, for example relative to the vertical. In the application described below with reference to FIGS. 6 to 12, the orientation information may be used in order to determine the configuration of the refractor and thus the type of acuity measurement (far vision, intermediate vision or near vision) currently being carried out.

The computing machine 66 receives the temperature information generated by the temperature sensor 62 and the orientation information generated by the inclinometer 64 and uses at least one of these pieces of information in the context of the computation of the commands to send to the motors 42, 44, 46.

In the example described, the control module 70 uses the temperature information in order to compensate for variations in the spherical power of the lens 6 due to temperature (about 0.06 D/° C. in the described example) and the orientation information in order to compensate for possible disturbance of the drive system (motors, grub screws, toothed wheels) due to changes in the orientation of the vision compensating device 10.

In contrast to the case described above with regard to FIGS. 2 to 4, the following description of FIGS. 6 to 12 refers to directions (horizontal and vertical directions especially) and relative positions ("lower" or "upper") that correspond to conventional use of a refractor to measure the visual acuity of a patient.

Figure 6:
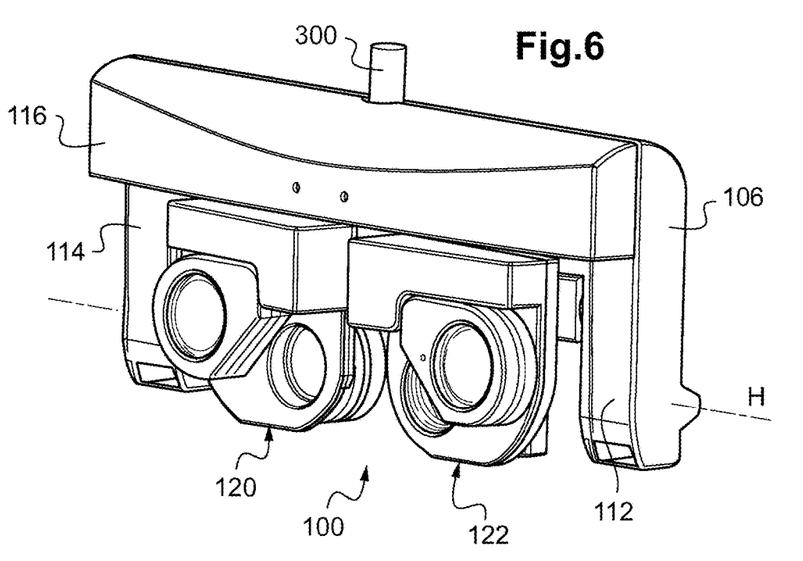
FIG. 6 is a perspective view of a refractor according to the teachings of the invention in a first configuration intended for testing far vision.
Figure 7:
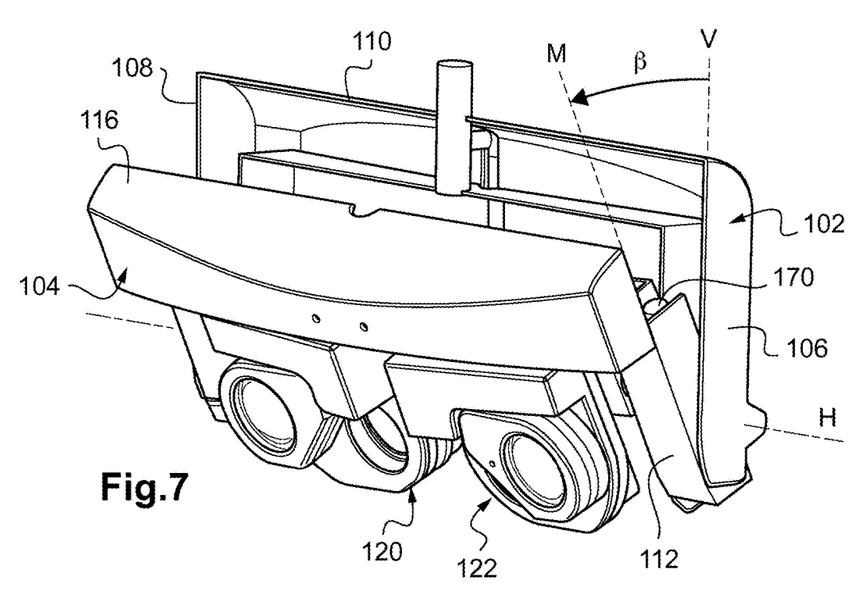
FIG. 7 is a perspective view of the refractor in FIG. 6 in a second configuration intended for testing near vision.

FIGS. 6 and 7 show, in perspective, a refractor 100 according to the teachings of the invention, in a first configuration intended to test far vision and in a second configuration intended to test near vision, respectively, it being understood that the refractor may also take any intermediate position.

The refractor 100 comprises a stationary portion 102, intended to be mounted on a refraction-head holder, and a movable portion 104 forming an orientable holder, which portion is mounted on the stationary portion 102 so as to be rotatable about a horizontal axis H, for example over a given angular range.

The stationary portion 102 here has a gantry shape and comprises two vertical parallel risers 106, 108 and a horizontal beam 110 joining the two risers 106, 108 in their upper portion, and via which the stationary portion 102 may be mounted on the refraction-head holder, a portion 300 of which may be seen in FIGS. 6 and 7.

In the embodiment described, the orientable holder 104 also has a gantry shape and thus comprises two parallel risers 112, 114 and a crosspiece 116 that joins the two risers 112, 114 in their upper portion.

The riser 106 of the stationary portion 102 and the riser 112 of the orientable holder 104 comprise complementary means for guiding rotation about the horizontal axis H (see the reference 113 in FIG. 10), said means here being located in the lower region of these risers 106, 112.

Likewise, the riser 108 of the stationary portion 102 and the riser 114 of the orientable holder 104 comprise complementary means for guiding rotation about the horizontal axis H (see the reference 115 in FIG. 10), said means here being located in the lower region of these risers 108, 114.

Thus, the orientable holder 104 is movable, relative to the stationary portion 102 and about the horizontal axis H, between a position in which its risers 112, 114 are vertical (illustrated in FIG. 6) and a position in which its risers 112, 114 are inclined at an angle of inclination β relative to the vertical V (illustrated in FIG. 7), with here β=30°.

The orientable holder 104 may be positioned in one or more intermediate positions between these two positions.

The movement of the orientable holder 104 relative to the stationary portion 102 is here motorized: a grub screw driven by a motor 170 (clearly shown in FIG. 10) securely fastened to the orientable holder 104 for example engages with a pinion segment securely fastened to the stationary portion 102.

As a variant, the orientable holder 104 could be moved manually relative to the stationary portion 102; provision may then be made for mechanical means allowing the rotation to be stopped in one or more positions of the orientable holder 104 relative to the stationary portion 102.

The risers 106, 108 of the stationary portion 102 here have substantially the same exterior shape as the risers 112, 114 of the orientable holder 104, respectively; the riser 106 of the stationary portion 102 is furthermore placed in line with the riser 112 of the orientable holder 104 and the riser 108 of the stationary portion 102 is located in line with the riser 114 of the orientable holder 104. Moreover, the beam 110 of the stationary portion 102 is located in line with the crosspiece 116.

In addition, provision is made here for the structural elements of the stationary portion 102 (i.e. the risers 106, 108 and the beam 110) to be hollow in order to receive the corresponding elements of the orientable holder 104 (i.e. the risers 112, 114 and the crosspiece 116, respectively) when the latter is in its vertical position, as illustrated in FIG. 6.

Figure 8:
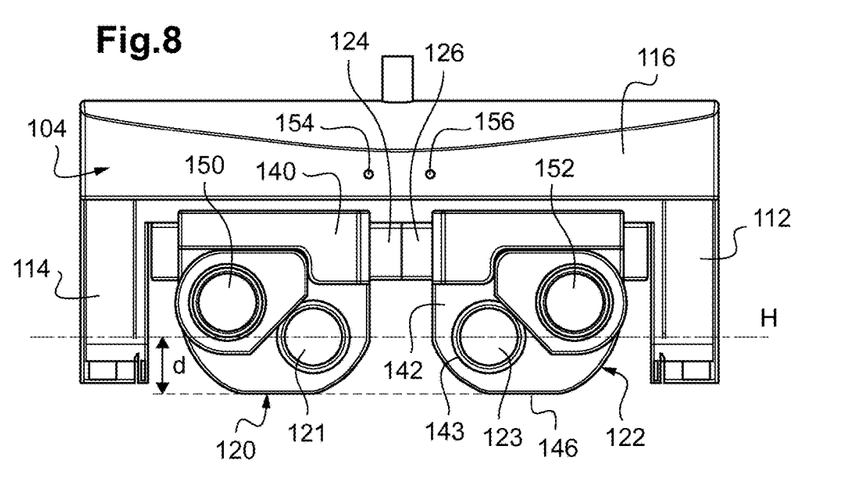
FIG. 8 is a front view of the refractor in FIG. 6, seen from the operator side.
Figure 9:
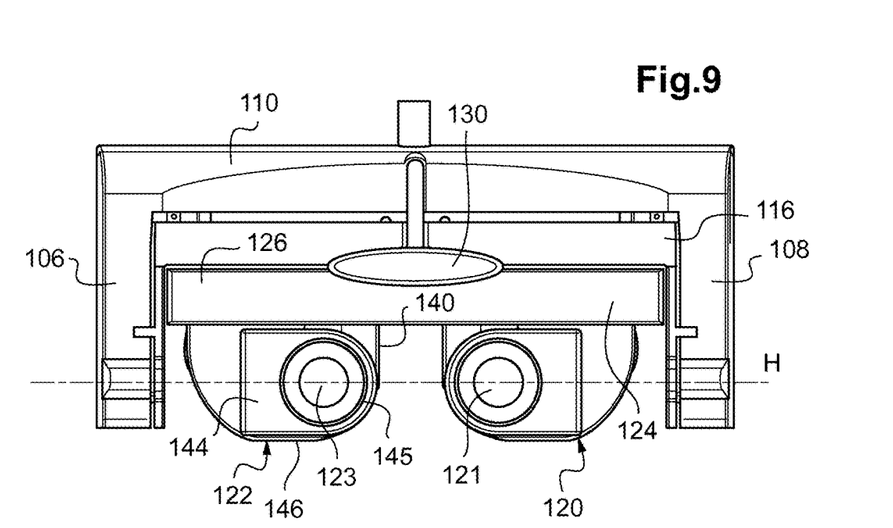
FIG. 9 is a front view of the refractor in FIG. 6, seen from the patient side, i.e. from the side opposite the view shown in FIG. 8.

FIGS. 8 and 9 are front views of the refractor just described, seen from the operator side and from the patient side, respectively.

As may be clearly seen in these figures, the refractor 100 comprises a first vision compensating subsystem 120 comprising an eyepiece 121 intended for the right eye of the patient and a second subsystem 122 comprising an eyepiece 123 intended for the left eye of the patient.

The first subsystem 120 is mounted (so as to be translationally movable horizontally as described below with reference to FIG. 11) on a first hinged arm 124 that extends parallel to the crosspiece 116, approximately over half the length of the crosspiece 116.

The first hinged arm 124 is mounted on the crosspiece 116, in the end region of the latter, i.e. near the riser 114, so as to be rotatable about an axis M that extends in the general direction of extension of the riser 114, as explained below with reference to FIG. 10.

The first hinged arm 124 is mounted under the crosspiece 116 and the first subsystem 120 is mounted on the first hinged arm 124 so as to extend, essentially, under the first hinged arm 124. In particular, the eyepiece 121 of the first subsystem 120 is located in its entirety under the first hinged arm 124.

Similarly, the second subsystem 122 is mounted (so as to be translationally movable horizontally as described below with reference to FIG. 11) on a second hinged arm 126 that extends parallel to the crosspiece 116, approximately over the other half of the length of the crosspiece 116.

The second hinged arm 126 is mounted on the crosspiece 116, in the end region of the latter (opposite the region in which the first hinged arm 124 is mounted), i.e. near the riser 112, so as to be rotatable about an axis that extends in the general direction of extension of the riser 112, as explained below with reference to FIG. 10.

The second hinged arm 124 is mounted under the crosspiece 116 and the second subsystem 120 is mounted on the second hinged arm 126 so as to extend, essentially, under the second hinged arm 126. In particular, the eyepiece 123 of the second subsystem 122 is located in its entirety under the second hinged arm 126.

More precisely, the respective centres of the eyepieces 121, 123 of the first and second subsystems 120, 122 are located in the horizontal plane containing the horizontal axis H of rotation of the orientable holder 104 relative to the stationary portion 102.

As may be clearly seen in FIG. 9, the stationary portion 102 also bears means for positioning the head of the patient 130, generally designated a "forehead rest", the position of which is optionally adjustable translationally in the vertical direction (i.e. parallel to the vertical axis V).

Here it is proposed that the refractor be dimensioned such that the horizontal axis H passes through the centres of rotation of the eyes of the patient.

Thus, when the patient has his head positioned against the positioning means with his eyes facing the eyepieces 121, 123, the eyepieces 121, 123 of the subsystems 120, 122 hardly move at all when the orientable holder 104 is inclined relative to the stationary portion 102, this movement furthermore following the gaze of the patient (especially when the latter lowers his gaze for near vision).

Each subsystem 120, 122 comprises a plurality of elements protected by an enclosure 140 especially formed from a front face 142, a back face 144 and a lower face 146. Each subsystem 120, 122 especially comprises a vision compensating device 200 such as described above with reference to FIGS. 1 to 5.

The front face 142 and the back face 144 each contain an optical window 143, 145 that delimits (in each face 142, 144) the eyepiece 121, 123 of the subsystem in question 120, 122.

The subsystem 122 is described in detail below with reference to FIG. 12. The subsystem 120 is of similar construction (the two subsystems 120, 122 being symmetric about a vertical plane passing through the middle of the crosspiece 116).

By virtue of the limited bulk of the vision compensating device 200 described above with reference to FIGS. 1 to 5, the lower face 146 of each subsystem 120, 122 is located near the optical axis of the vision compensating device in question (in other words the centre of the eyepiece 121, 123 in question). Thus, because of the construction adopted, as indicated above (axis of rotation H at the centres of the eyepieces 121, 123), the lower face 146 of each subsystem 120, 122 is located near (for example located at a distance d smaller than or equal to 30 mm or less, preferably smaller than or equal to 20 mm—here equal to 20 mm, in projection onto a vertical plane) the axis of rotation H of the orientable holder 104 relative to the stationary portion 102.

Thus, the orientable holder 104, and in particular the subsystems 120, 122, do not interfere with the face of the user when the orientable holder 104 is rotated about the horizontal axis H in order to pass from the configuration suitable for measuring far vision (FIG. 6) to the configuration suitable for measuring near vision (FIG. 7).

Each subassembly 120, 122 also comprises means for positioning a diasporameter 150, 152 that is movable between two separate positions on the front face 142: in a first position, the prisms of the diasporameter are aligned with the centre of the eyepiece 121, 123 in question, i.e. with the optical axis of the vision compensating device in question; in the second position, the diasporameter is positioned away from the eyepiece 121, 123 in question and leaves the optical window 143 free.

In the example described here, these positioning means are magnets borne by each diasporameter 150, 152 and intended to interact with magnetic elements (here magnets) of the subsystem 120, 122 in question, as explained below with reference to FIG. 12.

Each diasporameter 150, 152 comprises two rotatably guided frames that are toothed on their periphery and that bear, in a housing, a prism, the prisms of the two frames being aligned. Each frame may be rotated by a dedicated actuator, for example composed of a (stepper or DC) motor and a grub screw.

Each diasporameter 150, 152 may furthermore comprise an accelerometer in order to allow its specific position on the front face 142 of the enclosure of the subsystem in question 120, 122 to be determined.

As may be seen in FIG. 8, the orientable holder 104 comprises, for example in the central region of the crosspiece 116, an illuminating means 154 (for example an infrared emitter/receiver), in particular usable during the near-vision acuity measurement, and an emitter/receiver device 156 associated with an electronic control board 160 as explained below with reference to FIG. 10.

Figure 10:
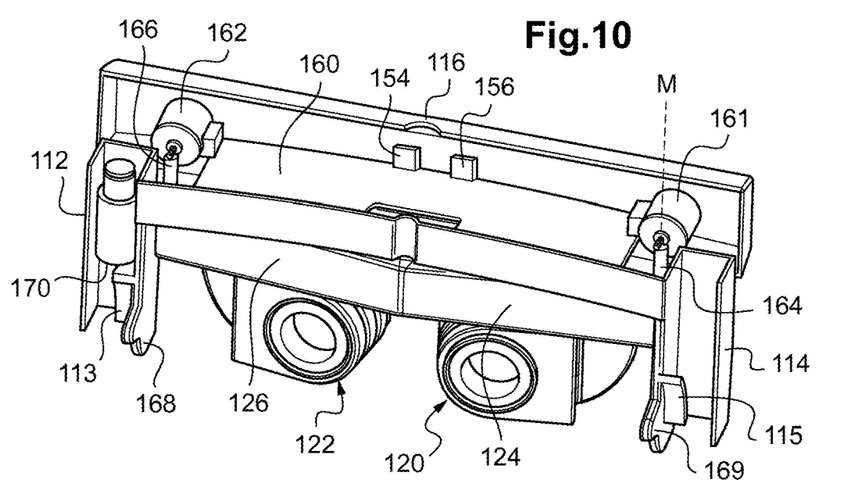
FIG. 10 is a cutaway view of the orientable holder of the refractor in FIG. 6.

FIG. 10 is a cutaway showing the orientable holder 104 in detail.

The crosspiece 116 houses the electronic control board 160 here placed horizontally and over almost all of the length of the crosspiece 116. The electronic control board 160 especially bears the illuminating means 154 and the emitter/receiver device 156, here making contact with a front face of the crosspiece 116, which is equipped with orifices in line with the illuminating means 154 and the emitter/receiver device 156, respectively.

The crosspiece 116 also houses, on either side of the electronic control board 160 (in the length direction of the crosspiece 116), a first motor 161 and a second motor 162, respectively: the first motor 161 allows the first hinged arm 124 to be driven to move about its axis of rotation 164 (oriented as already indicated in the direction M of extension of the riser 114); the second motor 162 allows the second hinged arm 126 to be driven to move about its axis of rotation 166 (parallel to the axis 164 of rotation of the first hinged arm and to the direction M).

Each of the first and second motors 161, 162 is mounted at one end of the electronic control board 160 and is controlled by the latter depending on instructions received via the emitter/receiver device 156.

As may be clearly seen in FIG. 10, the movement of the hinged arms 124, 126 due to actuation of the motors 161, 162 allows the optical axes of the subsystems 120, 122 (borne by the hinged arms 124, 126, respectively, as indicated above) to be made to converge, especially so as to accommodate near vision. It will be understood that the hinged arms 124, 126 may generally be moved forward or backward from the general plane of the refractor.

The angle of convergence Φ to be used for a measurement of visual acuity at a distance D (distance between the pupil and the acuity scale) and for a person having a monocular pupillary distance dPD for the eye in question is given by the formula: Φ=arctan(dPD/D).

In order to be able to accommodate the largest pupillary distances generally encountered (80 mm), and an observed object (acuity scale) at a distance D=350 mm, provision may for example be made for each subsystem 120, 122 to be able to rotate about the associated axis 164, 166 by as much as a limiting value comprised between 5° and 20°, here 6.5°.

The orientable holder 104 also bears (here inside the riser 112) the motor 170 that allows, as indicated above, the inclination of the orientable holder 104 to be adjusted relative to the stationary portion 102.

The motor 170 is also connected to the electronic control board 160 and may thus be controlled by instructions received via the emitter/receiver device 156. A coding system (coded wheel/sensor), also connected to the electronic control board 160, is optionally placed in the lower portion of the riser 112 in order to make it possible to know, continuously, the inclination of the orientable holder 104 relative to the stationary portion 102.

The electronic board 160 and the motors 161, 162, 170 are for example supplied with power by means of a supply circuit that is connected to the mains of the premises of the practitioner on the side of the stationary portion 102, and that joins the orientable holder 104 in the zone in which the orientable holder 104 is rotatably mounted on the stationary portion 102.

Each riser 112, 114 of the orientable holder 104 also bears an image capturing device 168, 169, here a video camera (for example using an infrared or visible CMOS sensor equipped with an objective) connected to the electronic control board 160 by a wired link, said image capturing device being mounted so that its line of sight is substantially parallel to the axis of rotation H of the orientable holder 104 relative to the stationary portion 102: each image capturing device 168, 169 thus has, in its field, a profile of the face of the patient level with the eye in question, and the back face 144 of the enclosure of the subsystem 120, 122 in question level with the eyepiece 121, 123 in question.

Thus, for the left eye and for the right eye, the electronic control board 160 may process the image taken by the image capturing device 168, 169 in question: on the one hand, this image may be transmitted via the emitter/receiver device 156 to an exterior system, such as a computer of the practitioner, in order for example to allow the practitioner to check that the eyes of the patient are indeed positioned in the centre of the eyepieces 121, 123; and on the other hand, the electronic control board 160 may measure, on the basis of this image, the distance between the top of the cornea of the eye in question and the back face 144 of the enclosure of the subsystem 120, 122 in question, in order possibly to correct the power setpoints of the vision compensating device in question to take account of this distance.

Specifically, taking the example of a spherical power S of equivalent focal length F, a positioning error ε would mean a corrected focal length F' would be required, equivalent to a spherical power S', where:

$$F' = F - \varepsilon \text{ and } S' = S\left(\frac{1}{1 - \frac{\varepsilon}{F}}\right),$$

which to a first approximation gives S'=S·(1+ε·S).

The electronic control board 160 will therefore transmit, to each of the vision compensating devices, spherical and cylindrical power setpoints that will depend not only on the spherical and cylindrical powers required by the practitioner, but also on the eye/device distance (here the cornea/back face 144 distance) measured by the image capturing device 168, 169.

Figures 11, 12:
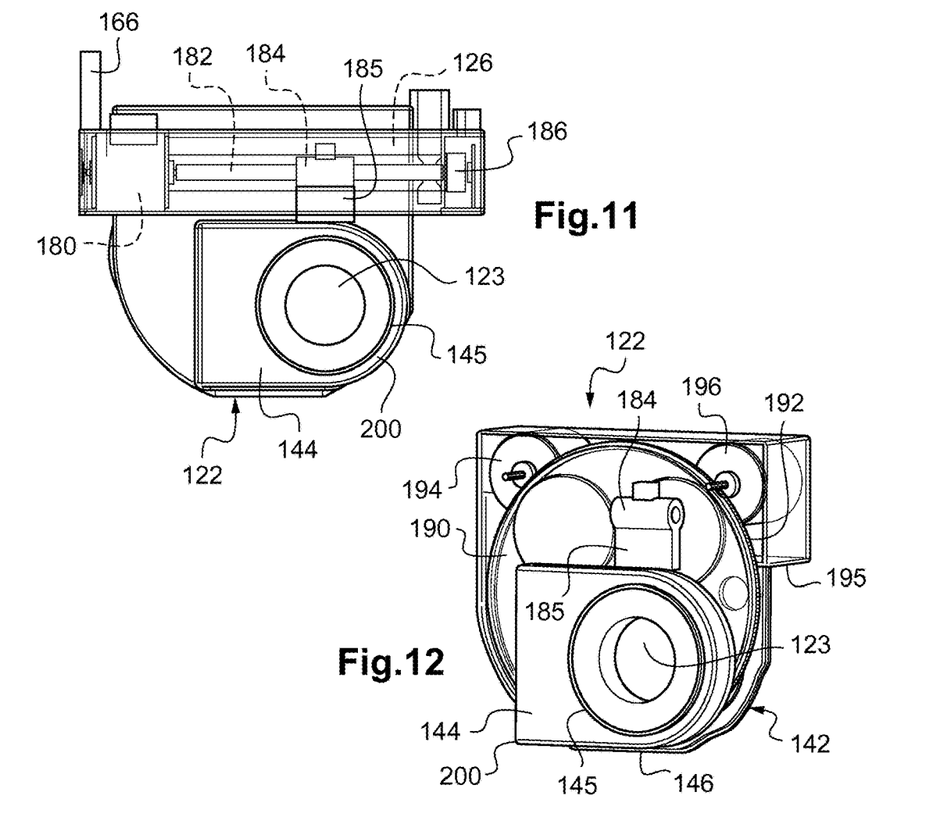
FIG. 11 is a detail view of a vision compensating subsystem mounted on a hinged arm in the refractor in FIG. 6.
FIG. 12 is a cutaway of the subsystem in FIG. 11.

FIG. 11 shows in detail how the subsystem 122 intended to measure the visual acuity of the left eye of the patient is mounted on the hinged arm 126.

The hinged arm 126 bears, at its external end (i.e. for the subsystem 122 intended for the left eye, its left-hand end as seen from the side of the patient and as illustrated in FIG. 11) a motor 180 (here a stepper motor) designed to rotate a threaded shaft 182 on which a slide 184 is mounted, said slide 184 being provided with an internal thread complementary to that of the threaded shaft 182.

The slide 184 is extended downward by an extension 185 that extends through a groove formed in the lower wall of the hinged arm 126, and at the lower end of which the subsystem 122 is mounted.

As will be described below with reference to FIG. 12, the subsystem 122 comprises a vision compensating device 200 such as that described above with reference to FIGS. 1 to 5, oriented so that its parallelepipedal space for receiving the motors is located laterally and to the exterior (here on the left as seen from the patient side) of its cylindrical space for receiving the optical elements, i.e. the eyepiece 123 (which corresponds to the optical window 145 formed in the back face 144 of the enclosure of the subsystem 122, which back face 144 is formed in this location by the casing 12 of the vision compensating device 200).

In other words, the vision compensating device 200 is positioned in the subsystem 122 so that the axis Z shown in FIGS. 2 to 4 is parallel to the horizontal axis of rotation H (the axis Y in FIGS. 2 to 4 being for its part parallel to the direction M of extension of the riser 112).

The subsystem 122 is precisely mounted on the extension 185 of the slide 184 level with the vision compensating device 200, in the junction portion between the parallelepipedal space for receiving the motors and the cylindrical space for receiving the optical elements.

The motor 180 is connected to the electronic control board 160 and may thus be controlled on the basis of instructions received via the emitter/receiver device 156. Moreover, a coding system 186 (coded wheel/sensor), also connected to the electronic control board 160 makes it possible to know precisely the angular position of the threaded shaft 182 and therefore the position of the slide 184 and of the subsystem 122.

Activation of the motor 180 causes the threaded shaft 182 to rotate and therefore the slide 184 and the subsystem 122 to move along the hinged arm 126.

Thus, the subassembly 122 may especially adopt two positions: an adjustable position tailored to the morphology of the patient (such that the eye of the patient and the eyepiece 123 are aligned) and a retracted position, in which the slide 184 is placed in its exterior end position (to the left in FIG. 11) and the subsystem 122 is therefore outside of the field of vision of the patient.

The retracted position may for example be used to measure the visual acuity of the patient without correction or to position the refractor at a height suitable for the patient (since the practitioner will then be able without difficulty to see the eyes of the patient), the subassembly 122 possibly then being subsequently moved into the working position.

As indicated above, the subsystem 120 is mounted on and moved over the hinged arm 124 in an analogous way to that described for the subsystem 122 on the hinged arm 126.

FIG. 12 shows the subsystem 122 designed to measure the visual acuity of the left eye of a patient.

As indicated above, this subsystem 122 especially comprises a vision compensating device 200 such as that described above with reference to FIGS. 1 to 5.

The subsystem 122 is moreover enclosed in an enclosure the back face 144 of which is formed by a portion of the casing 12 of the vision compensating device 200.

Between the vision compensating device 200 and the front face 142 of the enclosure (in the direction of the optical axis), the subsystem 122 bears an internal wheel 190 and an external wheel 192 that are centred on a common axis of rotation parallel to the optical axis and separate from the latter (the optical axis being that of the vision compensating device 200, i.e. that located at the centre of the eyepiece 123).

The internal wheel 190 for example bears a plurality of optical elements (for example a shielding portion, a polarizing filter, a colour filter, a Maddox filter, a decoupling prism) one of which may be selectively placed in front of the optical axis. The internal wheel 190 also contains a free passage that may also be positioned in front of the optical axis in order for the optical treatment provided by the subsystem 122 to correspond to that generated by the vision compensating device 200.

In the embodiment described here, in which the subsystem 122 bears on its front face 142 a diasporameter 152 that is movable over the front face 142, the external wheel 192 for example bears magnetic elements (here magnets) that interact, as indicated above, with magnets of the diasporameter so that moving the external wheel 192 about the aforementioned common axis moves the diasporameter 152 between its first position (in which the prisms are located on the optical axis) and its second position (in which the diasporameter leaves the field of view defined by the eyepiece 123 free).

The internal wheel 190 and/or the external wheel 192 are for example mounted in a removable casing equipped with a flap preventing ingress of dust. The practitioner may thus change the optical elements (filter, prism, shielding portion) present in the subsystem 122.

The front face 142 contains a projection 195 in order to decrease the volume of the lower portion of the subsystem 122 in order to limit the length of the optical path in the product to the benefit of the size of the field of view.

Specifically, the internal wheel 190 and the external wheel 192 are here equipped with teeth on their periphery, in which a pinion driven by a corresponding driving motor 194, 196 engages.

The driving motors 194, 196 are controlled by the electronic control board 160. An absolute coding system (not shown) makes it possible to reset the internal wheel 190 and the external wheel 192 independently.

By virtue of the adopted design, the subsystem 122 is small in size, typically smaller than 120 millimetres in height (i.e. in the direction M) and in width (i.e. in the direction H) and smaller than 60 mm in thickness (i.e. along the optical axis X of the vision compensating device 200); in the example described here, each subsystem is 80 mm in height, 80 mm in width and 43 mm in thickness.

An example use of the refractor described above will now be described.

The subsystems 120, 122 are initially positioned in their retracted positions (i.e. their horizontal positions furthest from a median vertical plane passing through the middle of the crosspiece 116). The orientable holder 104 is for its part in its vertical position (i.e. in the configuration of the refractor suitable for far vision, as shown in FIG. 6).

The patient then places his head in front of the refractor.

The practitioner may then adjust the height of the refractor using conventional means (not discussed here), the fact that it is possible to see the eyes of the patient because the subsystems 120, 122 are in their retracted position making this easier to do.

The patient then places his forehead on the positioning means 130 and the practitioner activates the motors 180 (for example using a computer that sends suitable instructions to the electronic control board 160) so as to move the subsystems 120, 122 horizontally along the hinged arms 124, 126 until the eyepieces 121, 123 are located facing the eyes of the patient.

The refractor is at this point configured to measure the visual acuity of the far vision of the patient.

The practitioner may then set (also by means of the computer, which emits instructions to the electronic control board 160) the positions of the various elements of each subsystem 120, 122 and in particular:

depending on the spherical and cylindrical correction setpoints received by the electronic control board 160 for a given eye, the electronic control board 160 passes setpoints to the vision compensating device associated with the eye in question, these setpoints taking into account, as indicated above, the distance between the eye and the vision compensating device measured by virtue of the image capturing device;

the electronic control board 160 optionally controls the rotation of the motor 194 in order to place, if needs be, an additional filter or prism on the optical axis; and the electronic control board 160 optionally controls the rotation of the motor 196 in order to place, if required, the prisms of the diasporameter 150, 152 in front of the eyepiece 121, 123 in question, and the rotation of the motors of the diasporameter 150, 152 in order to obtain the required prismatic correction.

When a suitable correction is found for the far-vision ametropia of the patient, the practitioner for example stores these (spherical, cylindrical and prismatic) correction values, in association with the current inclination of the orientable holder (for example determined by the electronic control board 160 by virtue of the coding system associated with the motor 170, or by the vision compensating devices 200 by virtue of orientation information delivered by the accelerometer), here an inclination of zero, in a memory.

The practitioner then makes the orientable holder 104 incline (by making it rotate relative to the stationary portion 102 about the horizontal axis H by means of the motor 170, which is controlled by the electronic control board 160 depending on instructions received via the emitter/receiver device 156 from the computer of the practitioner).

The refractor is then in its configuration in which the orientable holder 104 is inclined, for example by 30° relative to the vertical, in order to measure the visual acuity of the near vision of the patient. It will be understood that it is also possible to position the orientable holder 104 in other intermediate positions in order to measure an intermediate visual acuity.

As indicated above, because the horizontal axis H is placed level with the centre of rotation of the eye, the eyepieces 121, 123 follow the gaze of the patient and the refractor is therefore ready to measure the visual acuity of the near vision of the patient without him needing to reposition himself.

The practitioner may then set (as already explained above for far vision) the position of the various elements of each subsystem 120, 122.

When a suitable correction is found for the near-vision ametropia of the patient, the practitioner for example stores these (spherical, cylindrical and prismatic) correction values, in association with the current inclination of the orientable holder (for example determined by the electronic control board 160 by virtue of the coding system associated with the motor 170, or by the vision compensating devices 200 by virtue of orientation information delivered by the accelerometer), here an inclination of 30°, in a memory.

The correction values stored in memory (both for far vision and near vision and optionally for intermediate vision) will possibly then be used to produce ophthalmic lenses tailored to the sight of the patient.

The invention claimed is:

1. A refractor comprising:
   an enclosure comprising a front face containing a first optical window and a back face containing a second optical window aligned with the first optical window along an optical axis of observation thus forming an eyepiece for an eye of a patient; and
   at least one vision compensating device making it possible to observe along the optical axis of observation, wherein:
   the vision compensating device comprises, between the first window and the second window, a first optical element having a spherical power along the optical axis, said spherical power being variable; and wherein:
   said refractor comprises at least one image capturing device, in which the image capturing device is mounted in the refractor so as to measure the distance between an eye and the vision compensating device.

2. The refractor according to claim 1, in which the vision compensating device is designed to generate a cylindrical correction of variable cylinder axis and of variable power.

3. The refractor according to claim 1, in which the vision compensating device comprises a second optical element of cylindrical power and a third optical element of cylindrical power, the second optical element and the third optical element being rotatably adjustable about the optical axis independently of each other.

4. The refractor according to claim 1, comprising an orientable holder rotatable relative to a stationary portion about a horizontal axis, in which the enclosure is mounted on an arm hinged relative to the orientable holder about an axis perpendicular to the horizontal axis.

5. The refractor according to claim 1, comprising an orientable holder rotatable relative to a stationary portion about a horizontal axis, in which the enclosure is mounted on the orientable holder in a position that is adjustable along the horizontal axis.

6. The refractor according to claim 1, comprising an orientable holder rotatable relative to a stationary portion about a horizontal axis, in which a wheel is rotatably mounted in the enclosure about an axis parallel to the optical axis and bears at least one complementary element intended to be placed in front of the optical axis.

7. The refractor according to claim 1, comprising means for movably mounting a diasporameter on the front face of the enclosure in a first position, in which at least one prism of the diasporameter is aligned with the optical axis, and in a second position, in which the diasporameter leaves free the first optical window.

8. The refractor according to claim 1, in which the enclosure has a lower face and in which the distance, in projection onto a vertical plane, between the optical axis and the lower face is smaller than 30 mm.

9. The refractor according to claim 1, comprising an orientable holder rotatable relative to a stationary portion about a horizontal axis, in which the position of the orientable holder is rotatably adjustable about the horizontal axis by means of an actuator.

10. The refractor according to claim 1, comprising an orientable holder rotatable relative to a stationary portion about a horizontal axis, in which the stationary portion comprises means for positioning a portion of the head of a user.

11. The refractor according to claim 10, in which the stationary portion is dimensioned so that said horizontal axis passes through the eyes of said user.

12. The refractor according to claim 11, in which the stationary portion is dimensioned so that the horizontal axis passes through the centre of rotation of at least one eye of said user.

13. The refractor according to claim 1, in which the vision compensating device is designed to control the spherical power of the first optical element depending on the measured distance.

14. A method for measuring refraction by means of a refractor according to claim 1, said refractor comprising an orientable holder rotatable relative to a stationary portion about a horizontal axis, said method comprising the following steps:
  inclining the orientable holder relative to the stationary portion;
  adjusting the spherical power of the first optical element; and
  storing the adjusted spherical power in memory.

15. The measuring method according to claim 14, in which the spherical power is adjusted depending on the measured distance between the eye and the vision compensating device.

16. A refractor comprising:
  an enclosure comprising a front face containing a first optical window and a back face containing a second optical window aligned with the first optical window along an optical axis of observation,
  at least one vision compensating device making it possible to observe along the optical axis of observation,
  at least one image capturing device,
  an electronic control board,
  wherein the vision compensating device comprises an eyepiece and, between the first window and the second window, a first optical element having a spherical power along the optical axis, said spherical power being variable, wherein the image capturing device is mounted in the refractor so that a field of the image capturing device includes the eyepiece and an eye facing the eyepiece, and wherein the electronic control board is configured to process an image taken by the image capturing device and measure, on the basis of the image, a distance between the eye and the back face.

17. The refractor according to claim 1, wherein the at least one vision compensating device further comprises a ring and a motor that drives the ring to rotate, rotation of the ring thereby translating a part of the first optical element to vary said spherical power.

18. The refractor according to claim 17, further comprising a toothed wheel fastened to the ring, and wherein the motor includes a drive axis with a screw that is engaged with the toothed wheel to drive the toothed wheel and thereby rotate the ring.

* * * * *